United States Patent [19]

Bollin, Jr. et al.

[11] Patent Number: 4,485,176

[45] Date of Patent: Nov. 27, 1984

[54] TURBIDIMETRIC METHOD FOR MEASURING PROTEIN IN URINE AND CEREBROSPINAL FLUID

[75] Inventors: Ernest Bollin, Jr., Bear; Richard S. Schifreen, Wilmington, both of Del.

[73] Assignee: E. I. Du Pont de Nemours & Company, Wilmington, Del.

[21] Appl. No.: 392,784

[22] Filed: Jun. 28, 1982

[51] Int. Cl.³ .............................................. G01N 33/68
[52] U.S. Cl. ..................................................... 436/86
[58] Field of Search .............................. 436/86, 87, 97

[56] References Cited

U.S. PATENT DOCUMENTS 4,303,408 12/1981 Kim et al. .......................... 436/97 X

OTHER PUBLICATIONS

Iwata et al., Clinical Chemistry, 25, 1317, (1979).
Koreeda et al., J. Kyorin Med. Soc., 11, 371, (1980).

*Primary Examiner*—Arnold Turk
*Attorney, Agent, or Firm*—George A. Frank

[57] ABSTRACT

Improvements in the quantitative measurement of protein in urine and cerebrospinal fluid are provided by adding the assay reagents in two discrete steps and increasing the concentration of cationic surfactant. The method measures protein concentration based upon the turbidity produced in the presence of a cationic surfactant in an alkaline environment.

3 Claims, No Drawings

TURBIDIMETRIC METHOD FOR MEASURING PROTEIN IN URINE AND CEREBROSPINAL FLUID

TECHNICAL FIELD

This invention relates to a method for measuring protein in urine and cerebrospinal fluid and particularly to improvements in a method based on protein precipitation by cationic surfactants in an alkaline environment.

BACKGROUND ART

It is clinically important to measure protein levels in urine and other body fluids such as serum or cerebrospinal fluid as indicators of the status of patients in various disease states. High levels of protein in urine, for example, can be indicative of renal disease.

Several methods for determining the concentration of protein in urine or cerebrospinal fluid are known in the art. These involve the production of turbidity in acid or alkaline environments, the physical development or enhancement of a chromophore involved in dye binding to the protein, and the chemical generation of chromophores by known procedures such as the biuret or Lowry protein methods.

The biuret and Lowry procedures are generally recognized as being accurate, but are time-consuming and laborious. The other methods are more rapid and convenient, but are less accurate and more subject to interference.

A new method for the determination of protein in urine or cerebrospinal fluid has been described by Iwata, et al., Clinical Chemistry, Volume 25, 1317 (1979). In this method, the urine sample is diluted into a mixture of sodium hydroxide and ethylenediaminetetraacetic acid (EDTA). A cationic surfactant, benzyldimethyl{2-[2-(p-1,1,3,3,-tetramethylbutylphenoxy)ethoxy]ethyl} ammonium chloride (benzethonium chloride) is added immediately and mixed. After allowing the mixture to stand for 40–60 min, the absorbance is measured against water at 450 nm (for cerebrospinal fluid) or at 600 nm (for urine). The absorbance produced by the precipitated protein is compared to standards to determine the protein concentration in the body fluid.

Koreeda, et al., disclose a similar method for determining protein in urine, J. Kyorin Med. Soc., Volume 11, 371 (1980). In this procedure, the urine is diluted into a premixed solution containing sodium hydroxide, EDTA, and benzethonium chloride. The absorbance is measured at 660 nm after 20–40 min and is compared to standards to determine the protein concentration in the body fluid.

Although these two methods provide some improvement over the prior art, they still have several disadvantages. Spectrophotometric interference by sample chromophores and chemical interference by hydrophobic sample constituents such as bilirubin can distort the analysis and lead to false positive results. In addition, the reagent mixture described above is unstable and must be prepared daily. Furthermore, samples containing extremely high protein levels give rise to erroneously low assay values. Finally, the 20–60 min incubation times prior to the measurement of the absorbance are considered a disadvantage in the clinical laboratory.

There is a need for an assay for determining protein in urine and cerebrospinal fluid with improved rapidity and accuracy and which is less prone to interference.

DISCLOSURE OF THE INVENTION

The method of this invention for measuring protein levels in body fluids comprises the steps of mixing the body fluid with a chelator and a base, incubating the mixture for a finite period, adding a cationic surfactant in a concentration range of 4–13 mmol/L, and measuring the resulting turbidity.

DESCRIPTION OF THE INVENTION

The method of this invention is useful for measuring protein concentrations in body fluids, in particular urine and cerebrospinal fluid. The method is an improvement over the alkaline turbidimetric methods of Iwata, et al. and Koreeda, et al. described above. During an investigation of these methods, it was unexpectedly discovered that increasing the cationic surfactant concentration approximately tenfold and adding it to the reaction mixture separately and after a short delay provided surprising advantages over the prior art methods.

These advantages include: (1) shorter time to perform the assay; turbidity is generated and absorbance can be measured 26 to 120 seconds after adding the cationic surfactant; (2) prevention of erroneously low assay responses at extremely high protein levels; and (3) decrease in the interference caused by hydrophobic molecules such as bilirubin in the body fluid. It was also discovered that using a nonionic surfactant in the method of this invention increased the reproducibility of the absorbance measurements.

The method of this invention for measuring the level of protein in urine or cerebrospinal fluid comprises the steps of adding to the sample of urine or cerebrospinal fluid a chelator and base, in a separate step after a finite incubation period adding a cationic surfactant and then measuring the resulting turbidity. The speed of the assay can be improved by performing the steps at an elevated temperature in the range of 25°–40° C. The precision of the assay can be improved by adding a nonionic surfactant in the first step. The use of a blank measurement, i.e., performing all steps except adding the cationic surfactant, can help reduce assay interference from sample chromogens.

In a particularly preferred embodiment, the method of this invention for measuring levels of protein in urine comprises the steps of:

(1) diluting the urine sample into an aqueous solvent, preferably water or suitable buffer, in volume ratios of between 1 part urine to 9 parts water and 1 part urine to 99 parts water;

(2) warming the mixture to 30° C. or 37° C. and maintaining that temperature throughout all subsequent steps;

(3) adding, with mixing, a chelator, preferably EDTA, alkali, preferably NaOH, and nonionic surfactant, preferably Tween 20 (Tween is trademark or Atlas Powder Co., Wilmington, DE for general purpose emulsifiers which are poly(oxyethylene) derivatives of fatty acid partial esters of hexitol anydrides). The EDTA is preferably present at 6–12 mmol/L, NaOH at 131–417 mmol/L, and Tween at 0.1–0.28% (w/w);

(4) incubating for 20 seconds-4 minutes;

(5) adding, with mixing, a cationic surfactant, preferably benzethonium chloride at a concentration of 4–13 mmol/L;

(6) measuring the resulting turbidity in a photometer at a specified time from 20 to 270 seconds later, preferably at 540 nm;

(7) processing a sample blank as given in steps (1)–(6), except omitting step (5); and (8) subtracting the blank absorbance from step (7) from the test absorbance from step (6) and comparing the resulting difference to those obtained from processing a series of known standards.

The method of this invention is particularly useful for the measurement of protein in urine or cerebrospinal fluid performed on an automatic clinical analyzer (such as the aca TM discrete clinical analyzer available from E. I. du Pont de Nemours and Company, Wilmington, DE). Tests were performed on this instrument to compare the method of this invention to those described in the prior art. One important difference, leading to a dual advantage, between this method and prior methods is the concentration of the cationic surfactant, benzethonium chloride. The tenfold increase in benzethonium chloride concentration used in the method of this invention unexpectedly eliminated erroneously low assay responses at extremely high protein levels and reduced assay interference due to the presence of bilirubin in the sample.

Furthermore and even more surprisingly, the use of the separate and delayed addition of benzethonium chloride increased the sensitivity of the test system. In addition, by performing the assay at an elevated temperature, preferably 37° C., the time to measurement is shortened from 20–40 min to 26 to 120 seconds.

The examples which follow are illustrative of the invention.

EXAMPLE 1

Turbidimetric Measurement of Protein in Urine

The measurement of protein in urine was carried out of an automatic clinical analyzer (available from E. I. du Pont de Nemours and Company as the aca TM analyzer). The reagents for the assay were contained in an analytical test pack as described in U.S. Pat. No. Re. 29,725, issued Aug. 8, 1978 to D. R. Johnson, et al. which is hereby incorporated by reference. The analytical test pack for the urinary protein method contained 0.065 mL of 20% (w/v) ethylenediamine tetraacetic acid (EDTA) tetrasodium salt in water in dimple 1 (approximately 14 mg EDTA) 0.065 mL of 14 N sodium hydroxide in dimples 2 and 3 (approximately 73 mg NaOH), 0.040 mL of 24.9% (w/w) Tween 20 detergent in water in dimple 4 (approximately 10 mg of Tween 20) and 0.050 mL of 20% (w/v) benzethonium chloride in dimples 5 and 6 (approximately 20 mg benzethonium chloride). The blank analytical pack contained the same reagents in dimples 1, 2, 3, and 4 and no benzethonium chloride in dimples 5 and 6. The EDTA and Tween 20 solutions may contain thimerosal (0.005%, w/v) as an anti-microbial agent.

The test pack and blank pack were processed sequentially. A 0.400-mL aliquot of urine and a 4.6-mL aliquot of water were injected into each pack which was processed automatically in the aca TM analyzer. After 74 seconds of incubation to reach 37° C., the reagents in dimples 1 through 4 were added and mixed. After 216 seconds, the reagents in dimples 5 and 6 were added and mixed. After 39.5 seconds the aca TM analyzer automatically measured the absorbance at 540 nm. The result of subtracting the blank pack absorbance from the test pack absorbance was used to indicate the concentration of protein in the urine samples through a comparison of results with known standard protein solutions. These standards were prepared from human serum albumin diluted into a normal saline solution (0.9% sodium chloride, w/v) containing 0.4% Brij 35 and 0.005% thimerosal. The results of measurements on a series of these standards comprise a standard curve and the data for one standard curve are given in Table 1.

TABLE 1

| Standard Curve for Urinary Protein Method | |
|---|---|
| Protein Concentration (mg/L) | Absorbance at 540 nm (test pack minus blank pack) |
| 83 | 0.021 |
| 338 | 0.162 |
| 593 | 0.334 |
| 1418 | 0.737 |
| 2243 | 0.932 |

The urinary protein method of this invention compared acceptably to a reference method, an ethanolic phosphotungstic acid procedure, as described by Savory, et al. in Clinical Chemistry, Volume 14, No. 12, pages 1160 to 1171 (1968). Twenty-one random urine samples, tested by both procedures, gave the comparison data of Table 2. The analytical test packs used in this method comparison study did not contain Tween 20 in dimple 4 of the test packs; 0.300-mL samples of urine were used.

TABLE 2

| Comparison of Urinary Protein Method of this Invention to an Ethanolic Phosphotungstic Acid Method | |
|---|---|
| Number of Samples = | 21 |
| Slope = | 0.807 |
| Y-intercept[1] = | 1.9 |
| Correlation coefficient = | 0.984 |

[1]Y axis represents the method of this invention

The method of this invention gave good reproducibility as indicated in Table 3. Fifteen samples were processed sequentially at the indicated protein levels.

TABLE 3

| Reproducibility of Urinary Protein Method | |
|---|---|
| Protein Concentration (mg/L) | Coefficient of Variation (%) |
| 83 | 1.5 |
| 338 | 0.8 |
| 593 | 0.7 |
| 1418 | 0.7 |
| 2243 | 1.0 |

The method described above has an analytical range of 60 to 2400 mg/L. Urine samples having protein levels above 2400 mg/L are relatively rare. However, this method can be utilized even for such uncommon specimens after dilution with water or saline.

EXAMPLE 2

Time Dependent Measurement Of Urinary Protein

A time study to ascertain reaction completion was carried out utilizing an aca TM analytical test pack as described in Example 1 but utilizing a 0.500-mL sample of urine containing approximately 900 mg/L of protein. The absorbance values measured at various times after the addition of benzethonium chloride are given in Table 4. It can be seen that the reaction was substantially complete after 31.5 seconds (96.9% of the value at 121.5 s). The standard timing on the aca ™ analyzer causes the measurement to take place 39.5 seconds after adding the benzethonium chloride. Upon longer incubation times at 37° C., the absorbance, due to turbidity, decreased, presumably due to protein destruction in the highly alkaline environment.

TABLE 4

Absorbance Values as a Function of Time After Benzethonium Chloride Addition

| Time (s) | Absorbance at 540 nm | % of Final Value |
| --- | --- | --- |
| 26.5 | 0.5801 | 96.4 |
| 31.5 | 0.5832 | 96.9 |
| 36.5 | 0.5863 | 97.4 |
| 41.5 | 0.5887 | 97.8 |
| 46.5 | 0.5912 | 98.2 |
| 121.5 | 0.6019 | 100 |

Example 3

Measurement of Urinary Protein in Presence of Bilirubin (One-stage Method)

The measurement of protein in icteric urine was performed by the current method and compared to the prior art method. Two sets of analytical test packs were prepared as given in Table 5.

TABLE 5

| | Test Pack Design* | | | |
| --- | --- | --- | --- | --- |
| | Design A Present Method | | Design B Prior Art Method | |
| Dimple # | Volume (μL) | Reagent | Volume (μL) | Reagent |
| 1 | 65 | 14 N NaOH | 65 | 14 N NaOH |
| 2 | 65 | 14 N NaOH | 65 | 14 N NaOH |
| 3 | 65 | 14 N NaOH | 65 | 14 N NaOH |
| 4 | 50 | 40% Benzethonium chloride | 12 | 20% Benzethonium chloride |
| 5 | — | — | — | — |
| 6 | — | — | — | — |
| 7 | — | — | — | — |

*EDTA (disodium salt) was added with the water diluent.

These analytical test packs were processed in an aca ™ analyzer such that the addition of the benzethonium chloride occurred simultaneously with the addition of the NaOH. The absorbance at 600 nm was measured approximately 4.5 minutes after adding the benzethonium chloride. These conditions and benzethonium chloride concentration in Design B closely corresponded to those disclosed by Iwata, et al. Design A differed only in using a benzethonium chloride concentration within the limits of this invention. No nonionic surfactant was present nor was a blank measurement utilized in this study.

Protein standards were prepared from normal human serum proteins diluted into 0.9% (w/v) saline containing 0.005% (w/v) thimerosal to give 266, 531, 1062, 2125, 4250, 8500, 17000, 25500 and 34000 mg/L protein. Urine was prepared from a control product to contain approximately 1440 mg/L protein and either no bilirubin or 10 mg/dL bilirubin. The bilirubin was added by adding 1/10 volume of a concentrated (100 mg/dL) bilirubin solution in 40% DMSO, 0.1 N Na$_2$CO$_3$ to the urine solution. The protein concentration from this solution was compared to the identical solution containing the DMSO/Na$_2$CO$_3$ solution but without bilirubin. These urine samples were processed and compared to the known standards to give a protein value. Table 6 gives the results and shows that Design A has much less interference from bilirubin than Design B.

TABLE 6

Protein Measurement in Urine With and Without Bilirubin

| Sample | Design A | Design B |
| --- | --- | --- |
| Urine | 1364 mg/L | 1363 mg/L |
| Urine plus bilirubin | 1359 mg/L | 1589 mg/L |
| % Error | −0.4% | +16.6% |

Example 4

Measurement of Urinary Protein in Presence of Bilirubin (Two-stage Method)

The measurement of protein in icteric urine was performed by the present method and compared to the prior art method with two reagent-addition stages. Two sets of analytical test packs were prepared as given in Table 7.

TABLE 7

| | Test Pack Design* | | | |
| --- | --- | --- | --- | --- |
| | Design C Present Method | | Design D Prior Art Method | |
| Dimple # | Volume (μL) | Reagent | Volume (μL) | Reagent |
| 1 | 65 | 14 N NaOH | 65 | 14 N NaOH |
| 2 | 65 | 14 N NaOH | 65 | 14 N NaOH |
| 3 | 65 | 14 N NaOH | 65 | 14 N NaOH |
| 4 | — | — | — | — |
| 5 | — | — | — | — |
| 6 | 50 | 40% Benzethonium chloride | 12 | 20% Benzethonium chloride |
| 7 | — | — | — | — |

*EDTA (disodium salt) was added with the water diluent.

These analytical test packs were processed in an aca ™ analyzer such that the addition of the benzethonium chloride occurred approximately 40 seconds after the addition of the NaOH. The absorbance at 600 nm was measured approximately 4.5 minutes after adding the benzethonium chloride. These conditions and the benzethonium chloride concentration in Design D closely corresponded to those disclosed by Iwata, et al., except for the delayed addition of benzethonium chloride. Design C differed from Design D only in using a benzethonium chloride concentration within the limits of this invention. No nonionic surfactant was present nor was a blank measurement utilized in this study.

Protein standards were prepared from normal human serum proteins diluted into 0.9% (w/v) saline containing 0.005% (w/v) thimerosal to give 266, 531, 1062, 2125, 4250, 8500, 17000, 25500 and 34000 mg/L protein. Urine was prepared from a control product to contain approximately 1440 mg/L protein and either no bilirubin or 10 mg/dL bilirubin. The bilirubin was added by adding 1/10 volume of a concentrated (100 mg/dL) bilirubin solution in 40% DMSO, 0.1 N Na$_2$CO$_3$ to the urine solution. The protein concentration from this solution was compared to the identical solution containing the DMSO/Na$_2$CO$_3$ solution but without bilirubin. These urine samples were processed and compared to the known standards to give a protein value. Table 8 gives the results and shows that Design C has much less interference from bilirubin than Design D.

TABLE 8

| | Protein Measurement in Urine With and Without Bilirubin | |
|---|---|---|
| Sample | Design C | Design D |
| Urine | 1304 mg/L | 1364 mg/L |
| Urine plus bilirubin | 1340 mg/L | 1578 mg/L |
| % Error | +2.8% | +15.7% |

EXAMPLE 5

Measurement of Urinary Protein in Samples Containing a Wide Range of Protein Concentrations (One-stage Method)

The measurement of elevated levels of protein in urine was performed by the present method (one-stage) and compared to the prior art method.

Design A and B analytical test packs were prepared and processed as given in Example 3. Protein samples were prepared by diluting pooled human serum into saline to give protein levels of approximately 266, 531, 1062, 2125, 4250, 8500, 17000, 25500 and 34,000 mg/L.

The analytical test packs were processed as in Example 3 and the absorbance values at these protein levels are given in Table 9.

TABLE 9

| Protein Conc. | Measurement of Protein Absorbance at 600 nm | |
|---|---|---|
| (mg/L) | Design A | Design B |
| 266 | .022 | .020 |
| 531 | .056 | .048 |
| 1062 | .127 | .118 |
| 2125 | .265 | .193 |
| 4250 | .450 | .387 |
| 8500 | .602 | .545 |
| 17000 | .647 | .513 |
| 25500 | .628 | .178 |
| 34000 | .624 | .090 |

These results clearly show that packs based on prior art methodology (Design B) can give erroneously low test results for high protein content samples, whereas the present method (Design A packs) does not lead to absorbance values at high protein levels which could be confused with absorbance values resulting from those urine samples which actually contain much lower protein levels.

EXAMPLE 6

Measurement of Urinary Protein in Samples Containing a Wide-Range of Protein Concentrations (Two-Stage Method)

The measurement of elevated levels of protein in urine was performed by the present method (two-stage) and compared to the prior art method.

Design C and D analytical test packs were prepared and processed as given in Example 4. Protein samples were prepared by diluting pooled human serum into saline to give protein levels of approximately 266, 531, 1062, 2125, 4250, 8500, 17000, 25500 and 34,000 mg/L.

The analytical test packs were processed as in Example 4 and the absorbance values at these protein levels are given in Table 10.

TABLE 10

| Protein Concentration | Measurement of Protein Absorbance at 600 nm | |
|---|---|---|
| (mg/L) | Design C | Design D |
| 266 | .009 | .011 |
| 531 | .040 | .042 |
| 1062 | .114 | .118 |
| 2125 | .262 | .273 |
| 4250 | .495 | .504 |
| 8500 | .752 | .753 |
| 17000 | .918 | .749 |
| 25500 | .961 | .611 |
| 34000 | .896 | .159 |

These results clearly show that packs based on prior art methodology (Design D) can give erroneously low test results for high protein content samples, whereas the present method (Design C packs) does not give absorbance values at high protein levels which could be confused with absorbance values resulting from those urine samples which actually contain much lower protein levels. Thus, increasing the benzethonium chloride concentration eliminates this potential problem when a urine sample contains very high levels of protein in a two-stage assay.

The level of benzethonium chloride necessary to prevent these erroneously low results in the two-stage assay was identified by processing packs with varying concentrations of benzethonium chloride. These packs contained 24 mg of EDTA (50 $\mu$of 1.2 M tetrasodium salt) and 90 mg of NaOH but no detergent. A 0.300-mL sample of the high protein solution (35,000 mg/L) and a solution of 4,000 mg/L were processed. It can be seen in Table 11 that concentrations of benzethonium chloride lower than approximately 3 mmol/L will result in false results for high protein samples.

TABLE 11

| | Absorbance Values as a Function of Benzethonium Chloride Concentration | |
|---|---|---|
| Benzethonium Chloride | Absorbance at 540 nm | |
| Concentration (mmol/L) | 4,000 mg/L | 35,000 mg/L |
| 13 | 0.999 | 1.093 |
| 8.7 | 1.006 | 1.123 |
| 4.3 | 1.031 | 1.661 |
| 3.5 | 1.028 | 1.507 |
| 2.6 | 1.036 | 0.815 |
| 1.7 | 1.049 | 0.012 |
| 0.9 | 0.947 | 0.003 |

EXAMPLE 7

Improvement in Sensitivity in Two-Stage Assay

Using the benzethonium chloride concentrations of the current method, an improvement in sensitivity was demonstrated when the benzethonium chloride is added in a separate step after a delay of at least 20 seconds.

Analytical test packs were prepared as shown for Design A (one-stage) of Example 3 and Design C (two-stage) of Example 4. The reagent in dimple 6 (Design C packs) was added in a separate step after a delay of approximately 40 seconds. The protein standards were prepared as given in Example 3 and the packs were processed so that the measurements were made approximately 4.5 minutes after adding the benzethonium chloride.

The results, given in Table 12, indicate good sensitivity in the method of the present invention with the two-stage method showing better sensitivity (absorbance range of 0.887) than the one-stage method (absorbance range of 0.602).

TABLE 12

| Protein Concentration (mg/L) | Measurement of Protein Absorbance at 600 nm | |
|---|---|---|
| | One-Stage | Two-Stage |
| 266 | .022 | .009 |
| 531 | .056 | .040 |
| 1062 | .127 | .114 |
| 2125 | .265 | .262 |
| 4250 | .450 | .495 |
| 8500 | .602 | .752 |
| 17000 | .647 | .918 |
| 25500 | .628 | .961 |
| 34000 | .624 | .896 |

EXAMPLE 8

Measurement of Urine Absorbance in the Absence of Benzethonium Chloride

Analytical test packs were prepared as described in Example 1 but without benzethonium chloride. These blank packs were processed on an aca ™ analyzer with a 0.400-mL sample of urine. Table 13 shows the absorbance values at two wavelengths resulting from six randomly selected urine samples.

TABLE 13

| Absorbance Values of Random Urine Samples | | |
|---|---|---|
| Urine No. | Absorbance at | |
| | 540 nm | 600 nm |
| 73 | .022 | .012 |
| 89 | .013 | .007 |
| 90 | .028 | .017 |
| 92 | .007 | .003 |
| 94 | .012 | .006 |
| 95 | .011 | .005 |

These absorbance values correspond to protein levels approaching 100 mg/L (as seen by comparison to the standard curve of Table 1) and can result in significant test error. Therefore, absorbance values measured with such blank packs are subtracted from the absorbance value obtained when benzethonium chloride is present to yield a more correct value for the determination of protein concentrations in urine.

EXAMPLE 9

Effect of Surfactant on Sample Blank Measurements

Test packs were prepared and processed as described in Example 1 with various levels of nonionic surfactants placed in dimple 4. These packs contained no benzethonium chloride. The precision of the absorbance values resulting from the measurement of 0.300-mL samples of urine is shown in Table 14. The apparent useful concentration range for these surfactants is at least 0.06–0.23%

TABLE 14

| Effect of Surfactant on Sample Blank Measurement Precision | | | |
|---|---|---|---|
| Surfactant Concentration (%) | Standard Deviation seen with (n = 20) | | |
| | Brij-35 | Tween 20 | Triton X-100 |
| 0 | 1.1 | 1.1 | 1.1 |
| 0.06 | .5 | .3 | .3 |
| 0.12 | .4 | .3 | .3 |
| 0.23 | .5 | .3 | .3 |

We claim:
1. A method for measuring protein levels in urine or cerebrospinal fluid comprising the steps of mixing urine or cerebrospinal fluid, a base, EDTA and a nonionic surfactant, incubating the mixture for 20 seconds-4 minutes, adding benzethonium chloride in a concentration range of 4–13 mmol/L and measuring the resulting turbidity.

* * * * *